(12) United States Patent
Braithwaite

(10) Patent No.: US 6,347,629 B1
(45) Date of Patent: Feb. 19, 2002

(54) POWDER INHALER

(75) Inventor: Philip Braithwaite, Gloucestershire (GB)

(73) Assignee: Innovata Biomed Limited, Hertfordshire (GB)

( * ) Notice: Subject to any disclaimer, the term of this patent is extended or adjusted under 35 U.S.C. 154(b) by 0 days.

(21) Appl. No.: 09/336,244

(22) Filed: Jun. 18, 1999

(51) Int. Cl.$^7$ .............................................. A61M 15/00
(52) U.S. Cl. ........................ 128/203.15; 128/203.12; 128/200.18; 604/58
(58) Field of Search ................... 128/200.11, 200.14, 128/200.18, 203.12, 203.15, 200.23; 239/461, 468, 472, 466, 487, 489, 499, 371; 604/58

(56) References Cited

U.S. PATENT DOCUMENTS

| | | | |
|---|---|---|---|
| 4,907,583 A | 3/1990 | Wetterlin et al. | |
| 5,301,666 A | * 4/1994 | Perk et al. | 128/203.15 |
| 5,435,301 A | 7/1995 | Herold et al. | |
| 5,676,130 A | * 10/1997 | Gupte et al. | 128/203.19 |
| 6,240,918 B1 | * 6/2001 | Ambrosio et al. | 128/203.15 |

* cited by examiner

Primary Examiner—John G. Weiss
Assistant Examiner—Mital Patel
(74) Attorney, Agent, or Firm—Morse, Altman & Martin

(57) ABSTRACT

A dry powder inhaler comprises a body 1 defining a storage chamber for a powder and further defining an inhalation passage 2 through which air is drawn via a mouthpiece 3. A flow duct passing through the mouthpiece includes a circulatory section 25 in which the flow duct is in the form of one or more passageways. The flow duct further includes a cyclone chamber 35 between the circulatory section and the outlet of the mouthpiece.

6 Claims, 6 Drawing Sheets

Figure 1:
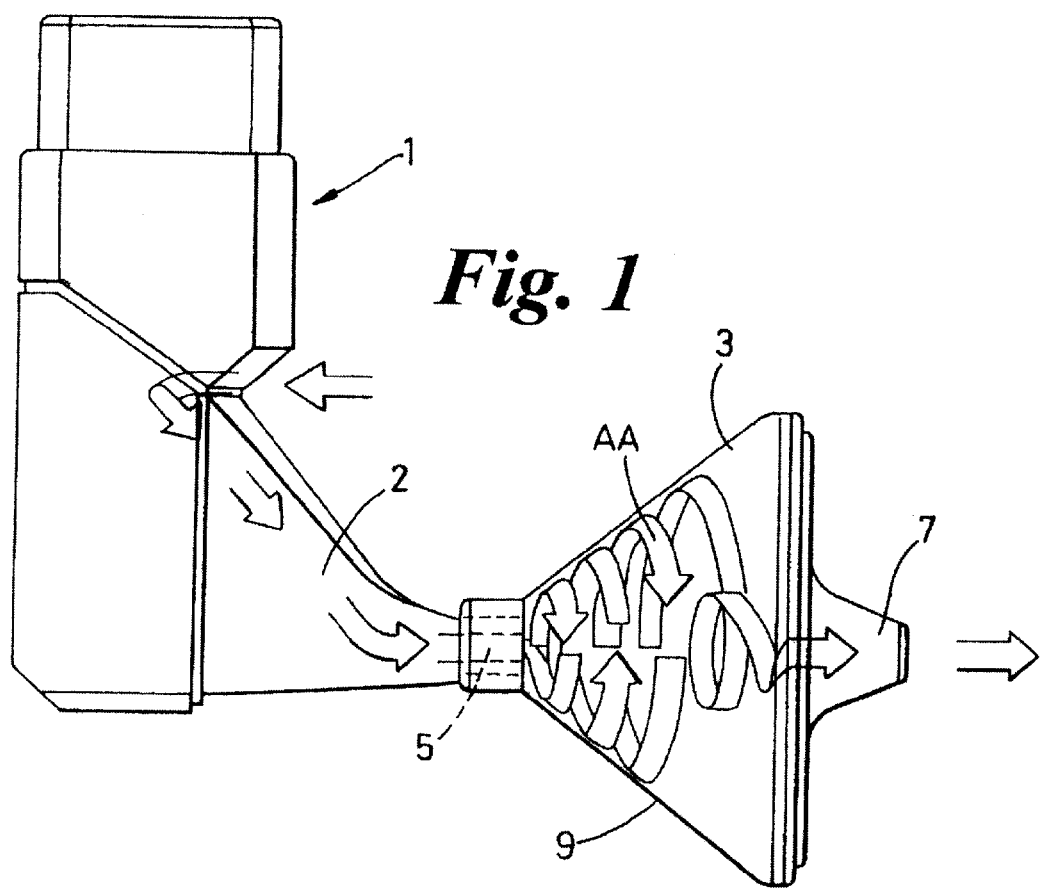

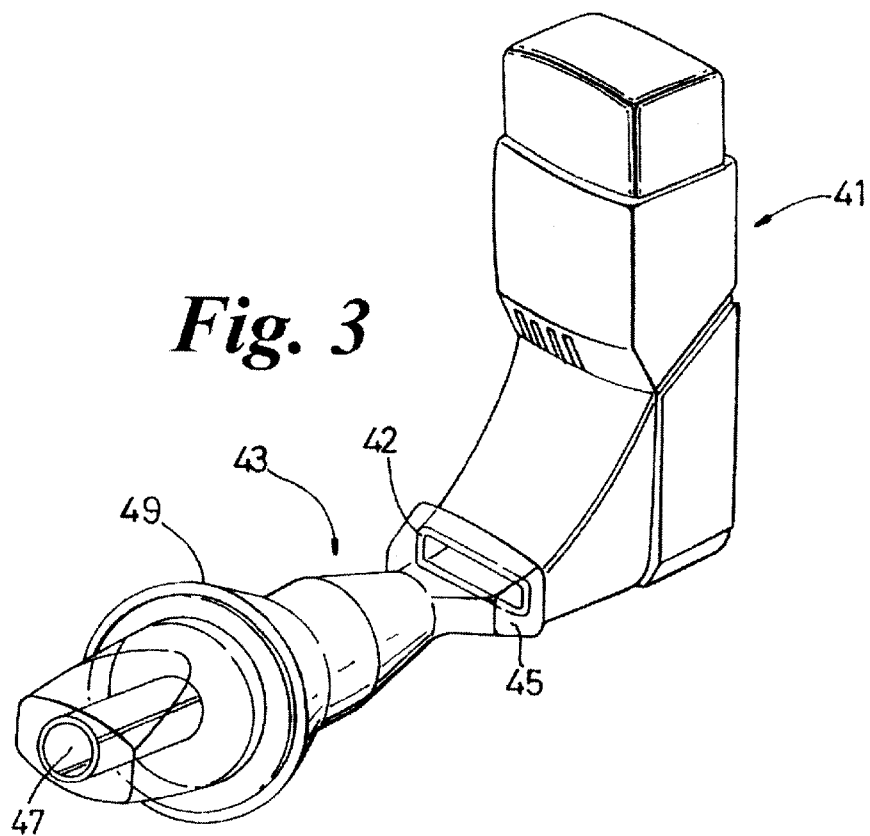
Fig. 3
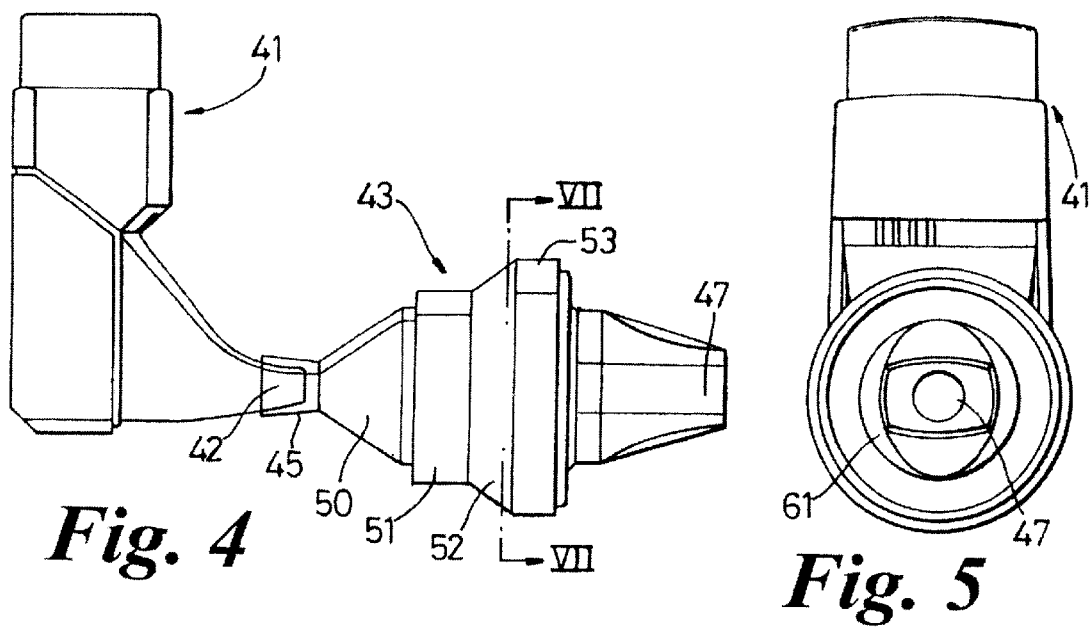
Fig. 4
Fig. 5

POWDER INHALER

BACKGROUND OF THE INVENTION

1. Field of the Invention

This invention relates to an inhaler whereby a drug in the form of a powder may be delivered to a patient.

2. Description of the Related Art

Inhalers are known which operate solely by the patient breathing in. The resultant inspired air carries the powder incorporating a medicament or drug into the lungs of the patient. An example of such an inhaler is described in EP-A-539469. The inhaler described in this patent specification comprises a body defining a storage chamber for the substance to be delivered and further defining an inhalation passage through which air is drawn via a mouthpiece. A metering member operates to transfer a volumetric dose of the substance from the storage chamber to the inhalation passage. The metering member is provided with dispensing cups and is moveable between a first position in which a dispensing cup is presented to the storage chamber to receive a dose of the substance to a second position in which a dose of the substance is presented to the inhalation passage.

Other dry powder inhalers are described in EP-A-0079478, EP-A-0166294, GB-A2165159, U.S. Pat. No. 2,587,215, U.S. Pat. No. 4,274,403 and EP-A-0069715.

The powder which is located in such dry powder inhalers may typically be a mixture of the medicament itself and a material such as lactose, the whole being in the form of a micronised powder. The presence of the lactose assists the free flow of the drug which might otherwise tend to agglomerate or adhere to the internal surfaces of the inhaler.

The formulation of the powder mix and the size of each dose are carefully controlled so that the desired amount of the powder, and therefore of the medicament, is of a size to reach the required area of the lungs. This amount is known as the respirable fraction. However, in use, a portion of the dose does not reach the lungs but remains in the throat of the patient. For some medicaments, this is undesirable and there is a in the throat of the patient. For some medicaments, this is undesirable and there is a need to provide an inhaler which is capable, in use, of retaining powder with a particle size above that of the respirable fraction rather than allowing such material to enter the patient's mouth.

There have already been proposals to deal with inhaler powders containing particles of relatively large size. For instance, WO-A-92/05825 describes a dry powder inhaler which includes a dispensing chamber into which the powder is introduced in operation. The dispensing chamber is connected via a duct to a mouthpiece through which the patient may inspire so as to cause air to flow through the chamber, the duct and then the mouthpiece. Within the duct there is located a stationary plate substantially transverse to the flow direction through the duct. As a result, substantially all the air flow through the duct is deviated abruptly to avoid the plate and the large particles impact with the plate due to their inertia. By such means the larger particles either break up or remain in the inhaler, reducing their delivery to the mouth and throat region of the patient, so reducing side-effects of the drug.

As indicated, devices such as those described in WO-A-92/05825 rely on one or more plates or baffles within the device to break up, or slow the progress of, larger particles. The small particles are able to change direction rapidly with the air flow and therefore pass through the device. A disadvantage of such a device is that its effectiveness depends on the period during which air is drawn through the device and the velocity of the air. There is a need for a device which is effective regardless of the air flow time and the air flow velocity.

It has also been proposed to use cyclonic separation of a larger particles from smaller particles to reduce the number of larger particles reaching the mouthpiece of the inhaler. The larger particles are of course heavier than the smaller particles so that when a mixture of the particles is introduced into a vortex or other cyclonic system the centrifugal forces then acting on the particles tend to throw the heavier particles further away from the centre of rotation of the system than the lighter particles. The use of a cyclonic system for holding back the heavier particles is exemplified by EPA-407028, which describes an inhaler in which an air/powder mixture is introduced into a cylindrical cyclone chamber through a tangentially disposed inlet. Air/powder mixture is withdrawn from the cyclone chamber by way of an outlet which is orthogonal to the inlet and lies on the axis of the cylindrical chamber. This arrangement is intended to select the smaller particles for inhalation. A comparable system is described in GB-A-1478138 which shows a powder inhaler provided with air inlets so arranged as to create a vortex within a powder storage chamber in order to trap heavier particles within the storage chamber while allowing lighter particles to escape into a housing for inhalation; this housing has air inlets adapted to create a vortex within the housing, which serves to throw heavier particles nearer to the wall of the housing than lighter particles so that they can be trapped and held back from leaving the housing.

Both baffle systems and cyclone systems can serve two purposes, firstly to break down agglomerated particles and secondly to trap agglomerates that have not been broken down. However, the design of such system for maximum efficiency in either of these respects is made more difficult by the limited nature of the power of suction that a typical patient is capable of applying to the mouthpiece. This difficulty is especially noticeable in the case of a cyclone system because the efficiency of a cyclone separator is dependent on the speed of circulation of the air/powder mixture, a speed which is largely determined by the velocity with which the air/powder mixture enters the cyclone chamber.

SUMMARY OF THE INVENTION

The present invention provides a dry powder inhaler comprising a body defining a storage chamber for a powder and further defining an inhalation passage through which air is drawn via a mouthpiece, the mouthpiece having an inlet and an outlet and defining a flow duct for the flow of an air/powder mixture therethrough, the flow duct extending between said inlet and said outlet and including a circulatory section (for effecting centrifugal separation of heavier and lighter particles) in which the flow duct is in the form of one or more passageways, said one or more passageways being circulatory about an axis extending between said inlet and said outlet, and the flow duct further including a cyclone chamber (for restraining heavier particles from reaching said outlet) between said circulatory section and said outlet.

The circulatory section of the flow duct serves primarily for effecting separation of heavier particles from lighter particles but also serves to convert the linear flow of the air/powder mixture entering the mouthpiece into a circulating flow in a smooth manner, with relatively little loss of kinetic energy, so that the air/powder mixture enters the cyclone chamber at relatively high speed.

Centrifugal forces act on the particles of the powder as the air/powder mixture circulates about the axis of the mouthpiece through the passageway(s) of the circulatory section. These forces set up a size distribution of particles across the passageway(s), the heavier particles being at the outside of the passageways, away from the axis of the mouthpiece, and the lighter particles at the inside of the passageway(s), towards the axis of the mouthpiece. Therefore, the powder enters the cyclone chamber with the lighter particles so positioned as to be preferentially drawn towards the centre of the chamber, from which air is being removed due to suction applied to the outlet of the mouthpiece by the patient. The heavier particles, on the other hand, remain in orbit in the chamber until the patient ceases to apply suction force.

In effect, the flow duct divides into two paths after the circulatory section. One path, followed by the lighter particles, leads to the outlet of the mouthpiece and to the patient, and the other path, followed by the heavier particles, leads to the radially outer region of the cyclone chamber. This maximises the proportion of lighter particles delivered to the patient, while minimising the proportion of heavier particles inhaled.

Earlier proposals to make use of cyclone chambers in powder inhalers have been for the purpose of effecting de-agglomeration, or for separating from one another the heavier and lighter particles of a powder in an air/powder mixture in which the particles have not previously been subjected to any separation and are still substantially uniformly distributed. In this invention the primary function of the cyclone chamber is not to effect de-agglomeration and/or separation but to retain in orbit the heavier particles which have previously been separated from the lighter particles by the circulatory section, thereby retaining them in the mouthpiece, to be discarded after the inhaler has been used. Some de-agglomeration of particles and some separation of particles may take place in the cyclone chamber but this is incidental and not essential. Accordingly, the term "cyclone chamber" is used herein to mean any chamber within which an air/powder mixture can be caused to circulate with an angular velocity generating centrifugal forces sufficient to maintain heavier particles of a powder mixture in orbit about an axis through the chamber.

The circulatory section of the flow duct may have any conformation adapted to effect circulatory flow of the air/powder mixture about the axis of the mouthpiece in such manner that the heavier and lighter particles of the powder are separated from one another by centrifugal forces.

The circulatory section is preferably a helical section in which the flow duct is in the form of one or more passageways of substantially helical conformation, preferably arranged as a helix or as helices about the aforementioned axis. Preferably the diameter of the or each helix increases in the direction from the inlet towards the outlet. The terms "helix" and "helical" are used to include both spiral and helical conformations, flat or extended, and with constant or variable diameters, and to include less than one turn and one or more turns.

Preferably, the cross-sectional area of each of the passageways in the circulatory section decreases in a direction from the inlet towards the outlet.

Preferably, the flow duct includes a section, located between the inlet and the helical section which is arranged so that the air/powder mixture flowing through the mouthpiece makes an abrupt change of direction. Accordingly the air/powder mixture encounters, in this section, a surface against which it impacts. This action causes agglomerated particles to break up.

Preferably the helical section of the flow duct terminates short of the outlet and the flow passage between said helical section and the outlet includes a section of cross-sectional area substantially less than the pitch circular diameter of the or each passage within the helical section. More preferably, said outlet section is located along the longitudinal axis of the helical section.

Preferably, the cyclone chamber extends, transversely of, for example at right angle to, the axis between the inlet and the outlet, the centre of the chamber preferably being on that axis.

Preferably, the flow duct is such that air passing from the helical section to the centrally located outlet section creates a Venturi effect producing a negative pressure in the outer chamber which serves to retain particles which have deposited in the chamber.

The present invention also provides a mouthpiece for a dry powder inhaler, the mouthpiece being for attachment to the body of the inhaler, and having an inlet and an outlet and defining a flow duct for the flow of an air/powder mixture therethrough, the flow duct extending between said inlet and said outlet and including a circulatory section in which the flow duct is in the form of one or more passageways, said one or more passageways being circulatory about an axis extending between said inlet and said outlet, and the flow duct further including a cyclone chamber between said circulatory section and said outlet.

BRIEF DESCRIPTION OF THE DRAWINGS

The invention will now be described, by way of example only, with reference to the accompanying drawings, in which:

FIG. 1 shows one embodiment of an inhaler of the present invention;

FIG. 2 is a longitudinal section of the inhaler of FIG. 1;

FIG. 3 is a perspective view of another embodiment of the invention;

FIG. 4 is a side-elevation view of the inhaler of FIG. 3;

FIG. 5 is an end view of the inhaler of FIG. 3;

FIG. 6 is a part-sectional view of the inhaler of FIG. 3;

FIG. 7 is a part-sectional view of the inhaler of FIG. 3, viewed along the lines VI—VI of FIG. 4;

FIG. 8 is a schematic view of some structural features of the inhaler of FIG. 3;

FIG. 9 shows another embodiment of the invention; and

FIGS. 9*a,* 9*b,* 9*c* and 9*d* show structural details of the inhaler of FIG. 9.

DETAILED DESCRIPTION OF THE PREFERRED EMBODIMENTS

Referring to the accompanying drawings, a dry powder inhaler 1 may be broadly similar to that described in EP-A-539469. It includes an integral tubular mouthpiece 2. In this embodiment of the present invention a further, separate mouthpiece device 3 is utilised in order to ensure that powder of a particle size greater than that which forms the respirable fraction does not enter the mouth of the user of the device.

Mouthpiece device 3 includes an inlet 5 into which the integral mouthpiece 2 of the inhaler 1 is engaged. Mouthpiece device 3 includes an outlet 7 through which the patient inhales in order to draw an air/powder mixture from inhaler 1, through mouthpiece device 3 and into the user's mouth.

Between inlet 5 and outlet 7, the mouthpiece device 3 includes a body portion 9 of substantially frusto-conical shape, the body portion 9 being arranged symmetrically about a straight line extending between inlet 5 and outlet 7 and having its narrow end joined to inlet 5.

Figure 2:
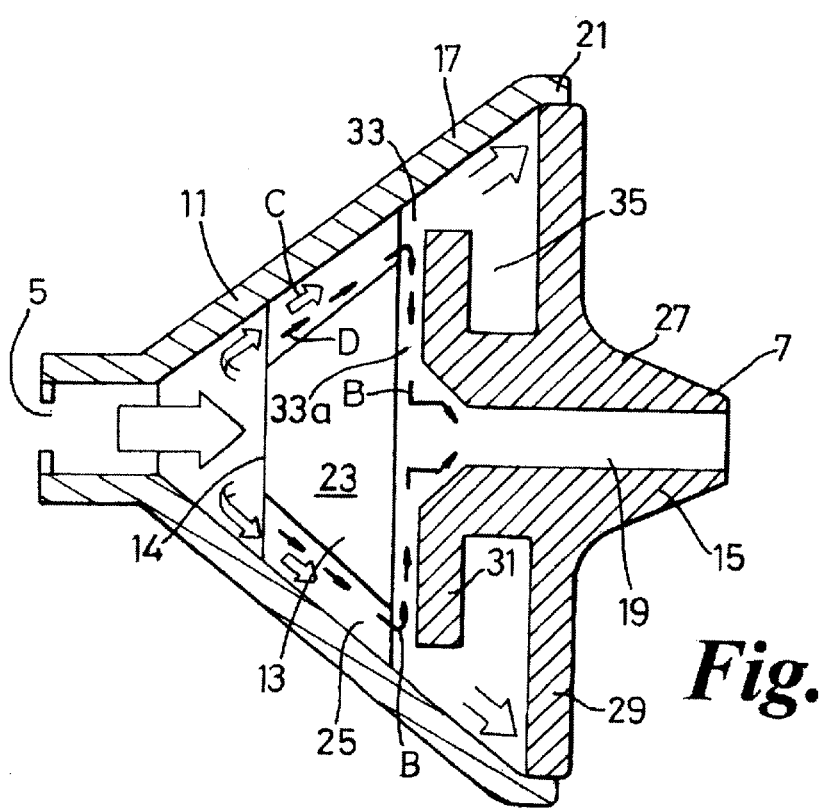

As best seen in FIG. 2, the mouthpiece device 3 is formed from three parts, 11, 13 and 15, each part being a moulded plastics item. Part 11 includes inlet 5 and, extending therefrom in a direction towards outlet 7, the outer frusto-conical wall 17 of the device. The second part 13 is an inner frusto-conical shaped member, the outer surface of which is dimensioned so that this part 13 may be fitted centrally within the first part 11 as indicated in FIG. 2. The third part 15 closes the wide end of the first part 11 apart from the provision of a central passageway 19 therethrough. Third part 15 includes outlet 7 and this part is dimensioned such that it may be pushed into firm engagement with an integral end flange 21 of first part 11, as shown in FIG. 2.

Mouthpiece device 3 provides a flow duct for an air/powder mixture from inlet 5 through to outlet 7. This flow duct is defined by the three parts of the device and follows a generally tortuous pathway, as will be described in detail below.

The second part 13 of the device is, as mentioned above, a generally frusto-conical member including a solid, frusto-conical shaped section 23 which is push-fit located in a central position within first part 11. Part 13 includes a flat surface 14 which faces towards inlet 5. After passing through inlet 5, the air/powder mixture first tends to strike the surface 14 which is located close to the inlet and blocking a direct flow path from the inlet 5 to outlet 7. This impingement of the air/powder mixture on surface 14 serves to break up any agglomerates of the particulate components of the powder which have not been broken up within the inhaler 1.

Between the central section 23 and the inner surface of wall 17 there is provided a helical section of the flow duct. In this helical section the flow duct is divided into a plurality of passageways of helical conformation, each helix being of increasing diameter as it extends across the helical section from the inlet end to the outlet end. As a result, the air/powder mixture is caused to spiral outwards and towards the mouthpiece of the device over this helical section, as shown schematically by the arrows AA of FIG. 1. The helical passageways within helical section 25 reduce in cross-sectional area at the outlet end, as a result of which the velocity of the air/powder mixture increases.

At the outlet end of the helical section 25, the air/powder mixture enters a region defined by all three parts of the device. The third part 15, which, as indicated above, forms a plug at the wide end of the first part 17, includes a central body portion 27 through which extends bore 19 forming the final section of the flow duct through the device. Extending radially outwardly from central body portion 27 are two integral, circular flanges 29 and 31. Flange 29 forms the outlet end wall of the device and engages the short flange 21 of first part 11. Flange 31 lies within the device, being spaced from flange 29 in a direction towards inlet 5. The outer peripheral edge of flange 31 is spaced from the inner surface of frusto-conical wall 17 of the first part 11 of the device. Flange 31 is also spaced longitudinally from the outlet end face of the second member 13.

As a result, there is defined by the three parts of the device a section 33 of the flow duct from the outlet end of the helical section 25 to the bore 19. Flow duct section 33 is largely formed by a gap 33*a* between flange 31 and the second part 13. The air mixture accordingly flows from the helical section into this gap moving radially inwardly and thence into bore 19 prior to entering the user's mouth, as shown by arrow AA of FIG. 1.

Retention of oversized particles within the device 3 is effected with the aid of centrifugal forces. Separation of the oversized particles from acceptably sized particles takes place in two stages, firstly within the helical section 25 and secondly within the flow path beyond the helical section.

Due to the helical path followed by the air/powder mixture in the helical section 25, as indicated in FIG. 1, the larger particles tend to be thrown to the outside of each helical passageway, The smaller particles tend to concentrate on the inside of each helical passageway as indicated by the solid arrows D in FIG. 2. When the air/powder mixture emerges from the helical section, the inner portion of it, which contains the smaller particles, tends to impinge on the outer part of flange 31 and therefore to follow the path of the flow duct as indicated by the solid arrows B in FIG. 2. In contrast, the outer portion of the air/powder mixture, which contains the larger particles, tends to continue along an outward spiral path (see outline arrows C in FIG. 2) and into a chamber 35 defined largely by the two flanges 29 and 31 and the frusto-conical wall 17.

Separation of oversized particles from acceptably sized particles thus takes place as a result of centrifugal forces acting on the powder within the helical section 25, and is in practice effective to ensure that few or none of the oversized particles find their way to the outlet 7, being instead diverted to the chamber 35. Some further separation of the oversized particles from any remaining acceptably sized particles takes place within the flow duct section 33 and the chamber 35 due to the fact that the air/powder mixture emerging from the helical section 25 and entering the chamber 35 establishes and maintains a spinning motion of the air within the flow duct section 33 and the chamber 35. The heaviest of the oversized particles accumulate at the base of the chamber. Less heavy oversized particles which continue to circulate within the spinning air are, however, held dynamically within the chamber 35, any acceptably sized particles may be entrained from the chamber 35 by the airflow towards the outlet 7. The chamber 35 and the flow duct section 33, including gap 33*a,* constitute a cyclone chamber for holding back larger particles, while permitting smaller particles to reach the outlet 7. When the patient ceases to inhale, the cyclonic motion of the air in the flow duct section 33 and the chamber 35 ceases and any powder which has been circulating with the air therein falls to the bottom of the chamber, from which it can be discarded in due course.

The bore 19 of the air duct is in the form of an orifice passing centrally through third portion 15. This orifice has a diameter substantially smaller than the pitch circular diameter of the helical section 25 at its outlet end. The air passing from the spiral passages into the orifice, which is initially convergent, creates a Venturi effect producing a negative pressure within chamber 35 which also serves to retain particles which are deposited in this chamber.

It will be appreciated that a mouthpiece device, such as that described above, may be integral with the main body of a dry powder inhaler rather than being a separate item attachable thereto.

FIGS. 3 to 8 show an inhaler 41 generally similar to the inhaler 1 of FIGS. 1 and 2, except that the inhaler 41 has a mouthpiece device 43 which differs from the mouthpiece 3 of inhaler 1.

The mouthpiece device 43 includes an inlet 45 into which the integral mouthpiece 42 of the inhaler 41 is engaged. Mouthpiece device 43 includes an outlet 47 through which the patient inhales.

Between inlet 45 and outlet 47 the mouthpiece includes a body portion 49 which includes a first frusto-conical section 50, a cylindrical section 51, a second frusto-conical section 52, and a second cylindrical section 53, all arranged symmetrically about an axis extending between inlet 45 and outlet 47.

Figure 6:
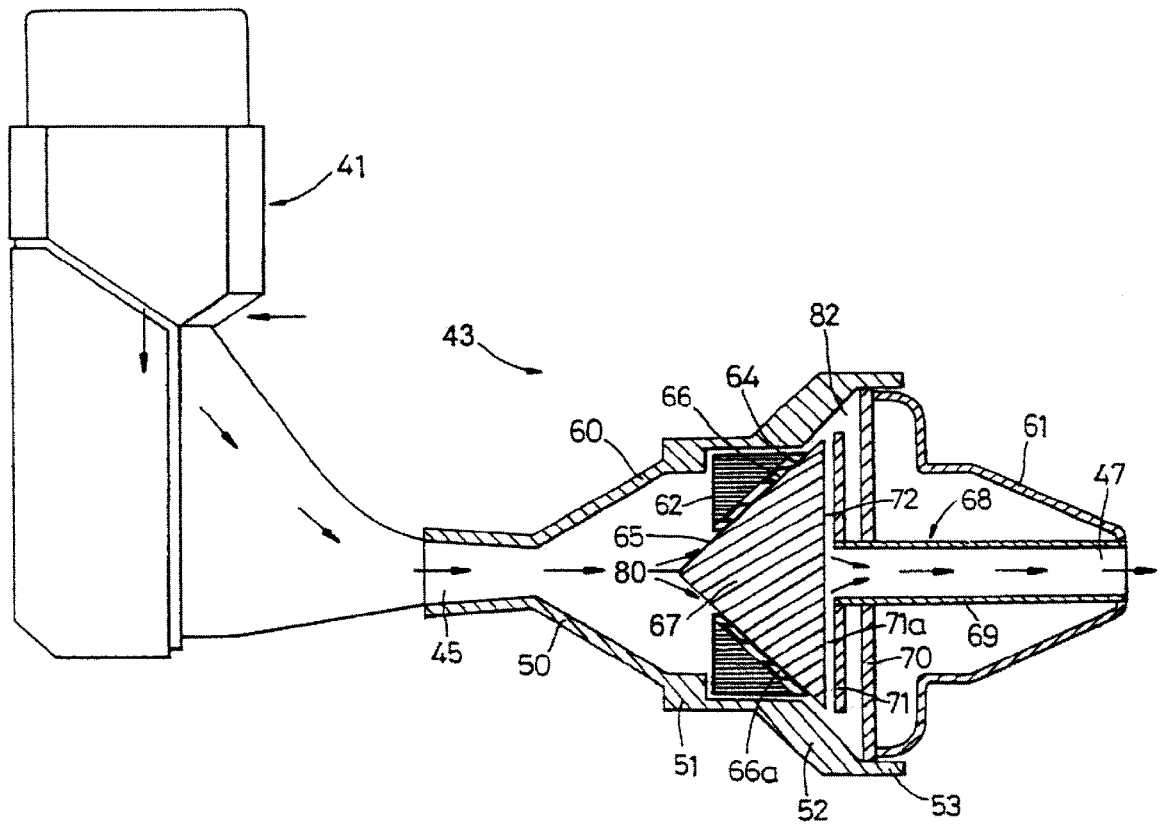
Figure 7:
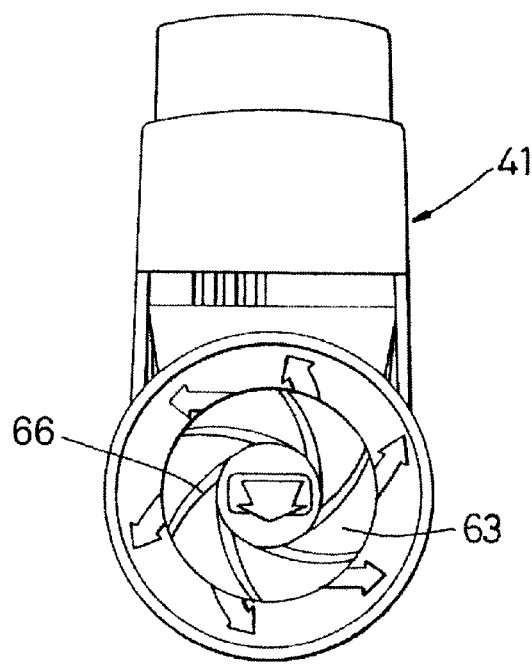

As best seen in FIG. 6, the mouthpiece device 43 is formed from five parts. Part 60 is a hollow moulding constituting sections 50, 51, 52 and 53 of body portion 49. Part 61 is a hollow cap which fits within the wider end of second cylindrical section 53 of body portion 49, and together with body portion 49 provides the outer surface of the mouthpiece device 43. Part 62 of the mouthpiece device is located largely within the first cylindrical section 51 and is in the form of a ring having an outer cylindrical wall (allowing the part to be a snug fit within section 5), a central aperture 65 and a frusto-conical inner wall 64, which is divergent from a central aperture 65 in the direction from the inlet 45 to the outlet 47 and has helical grooves 66 formed in its surface. Part 67 is a solid frusto-conical member shaped to fit within the frusto-conical inner wall 64, thereby blocking off the open tops of the helical grooves 66. Part 67 thereby combines with the inner wall 64 of part 62 to form helical passageways 66a extending from the aperture 65 to the interior of second frusto conical section 52.

Part 68 of the mouthpiece device is located largely within part 61 and is made up of a tubular section 69 through which air is drawn by the patient; it is integral with two circular flanges 70 and 71. Flange 70 is fixed to the inner surface of wider end of part 61. Flange 71 is axially spaced from flange 70. It is also spaced from the face 72 of the wider end of the frusto-conical part 67, to define an annular space 71a, by means of integral lugs (not shown) projecting from the face of the flange 71 and serving also to hold the part 67 in firm contact with the frusto-conical inner wall 64 of the part 62. The flange 71 is of smaller diameter than the flange 70, and is spaced at its perimeter from the inner wall of the second cylindrical section 53.

Figure 8:
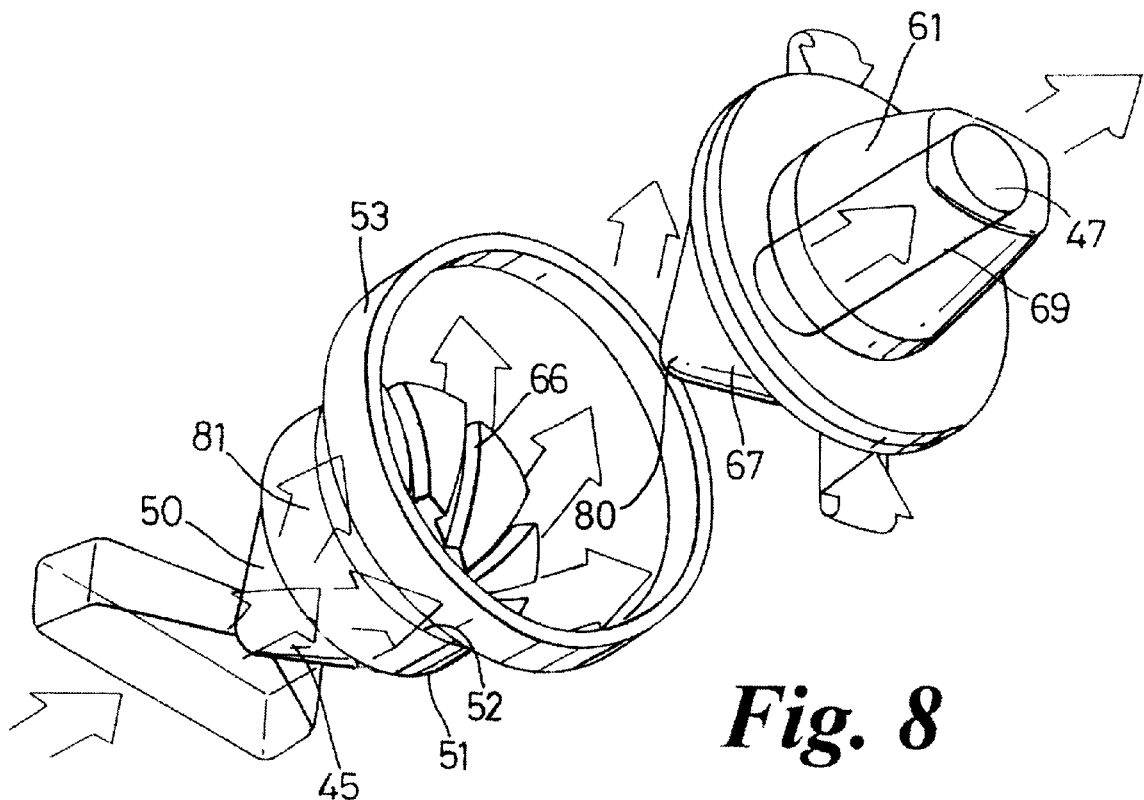

In use, the operation of the mouthpiece device 43 is similar to that of the mouthpiece device 3 of FIGS. 1 and 2. Suction applied by the patient to outlet 47 causes air/powder mixture to be drawn into the device through inlet 45. Some of this mixture strikes the exposed surface 80 of the frusto-conical part 67, which causes some breakdown of agglomerates. However, this effect is less pronounced than in the mouthpiece device of FIGS. 1 and 2 because the exposed surface 80 is smaller than the flat face 14 so that less of the incoming air/powder mixture strikes it. However, although the de-agglomerating effect is less, there is also less loss of kinetic energy and the speed of flow of the air/powder mixture is less reduced. This increases the efficiency of the subsequent cyclonic separation of the heavier and lighter particles in the mouthpiece device. The outline arrows 81 in FIG. 8 schematically indicate that much of the air/powder flow through the inlet 45 does not strike the flat face 80.

The air/powder mixture flows through aperture 65 into the helical passageways 66a and emerges therefrom tangentially into a cyclone chamber 82 bounded mainly by the inner wall of the second cylindrical section 53, the face 72 of the frusto-conical part 67, and the flange 70. The flange 71 is within this chamber; together with the face 72 it defines an annular space 71a.

The air/powder mixture emerges from the helical passageways 66a into chamber 82 with a speed and direction such as to set up cyclonic motion in chamber 82. During the passage of the air/powder mixture through the helical passageways 66a centrifugal forces cause the heavier particles to be thrown outwardly to a greater extent than the lighter particles. The mixture therefore enters the cyclone chamber 82 in streams which contain the lighter particles nearer to the axis of the chamber and the heavier particles nearer the inner wall of the second cylindrical section 53. The lighter particles are therefore better positioned to enter the annular space 71a from which they can pass to the outlet 47. The heavier particles on the other hand are restrained dynamically by centrifugal force from entering the annular space 71a and are held in orbit within the chamber 82 until such time as the patient ceases to inhale. If the powder contains a high proportion of heavier particles, such particles displace one another towards the flange 70 and may then build up in the space between the flanges 70 and 71, which thus serves as a trap to prevent a build-up of heavier particles about the perimeter of the annular space 71a. The passage of air from the chamber 82 to the outlet 47 creates a negative pressure in the space between flanges 70 and 71, which gives rise to forces serving to assist the centrifugal force in maintaining the heavier particles in orbit.

FIGS. 9, 9a, 9b, 9c and 9d show another embodiment of the invention. The inhaler 91 is similar to the inhaler of FIG. 1 but the mouthpiece device 93 differs from the mouthpiece device 3 of FIG. 1.

The mouthpiece device 93 comprises a disc 94, having a slot 94a, within which is fitted the outer wall of the inhaler mouthpiece 92, a cylindrical disc 95 having arcuate slots 96 in it, a cover disc 97, and a hollow cap 98 having an open-ended tubular extension 99.

Arcuate slots 96 are arranged in two pairs. Each slot 96a of a first pair extends from the periphery of disc 95 to a position close to the centre of the disc. Each slot 96b of the second pair extends from the periphery of disc 95 to a position about halfway between the periphery and the centre of the disc. The cylindrical disc 95 is adhesively secured to the slotted disc 94 with the slot 94a so aligned with respect to the slots 96 as to put each slot 96 into communication with the inhaler mouthpiece 92. As best seen in FIG. 9d, which shows disc 95 secured to disc 94, slot 94a and the arcuate slots 96 define four openings from inhaler mouthpiece 92 into the interior of mouthpiece device 93. Two openings 99 are located at opposite ends of elongated slot 94a and the two other openings 100 are located centrally with respect to slot 94a. between the periphery and the centre of the disc. The cylindrical disc 95 is adhesively secured to the slotted disc 94 with the slot 94a so aligned with respect to the slots 96 as to put each slot 96 into communication with the mouthpiece 92 of the inhaler. As best seen in FIG. 9d, which shows disc 95 secured to disc 94, slot 94a and the arcuate slots 96 define four openings from mouthpiece 92 of inhaler 91 into the interior of mouthpiece 93. Two openings 99 are located at opposite ends of elongated slot 94a and the two other openings 100 are located centrally with respect to slot 94a.

The cover disc 97 is adhesively secured to the cylindrical disc 95 and covers the open sides of the slots on the face of the cylindrical disc away from the disc 94. On the face of the cylindrical disc 95 adjacent disc 94 the open sides of the slots are covered by the adjoining face of the slotted disc 94, except where the slots 96 are in register with the slot 94a. In this manner there are formed spiral passageways 90 leading from the inhaler mouthpiece 92 to a cyclone chamber 100 bounded by the disc 94, the disc 97 and the cap 98. The conformation of the passageways 90 is that of a flat spiral rather than that of a helix.

As the air/powder mixture is drawn into the mouthpiece device from the inhaler 91 it passes through the slot 94a into the spiral passageways 96 where it is caused to circulate about the longitudinal axis of the mouthpiece device and is discharged from the passageways 96 tangentially into a cyclone chamber 100. The lighter particles of the powder can find their way to the patient's mouth by passing through the space 101 between the disc 97 and the inner wall of the cap 98 to reach the open end of the tubular extension 99. By contrast, the heavier particles are retained within the chamber 100 by centrifugal forces. When the patient ceases to exert suction, the heavier particles fall to the bottom of the chamber 100. The cap 98 is removable so that the retained heavier particles can be thrown away from time to time or if desired after every use of the inhaler.

Figure 9:
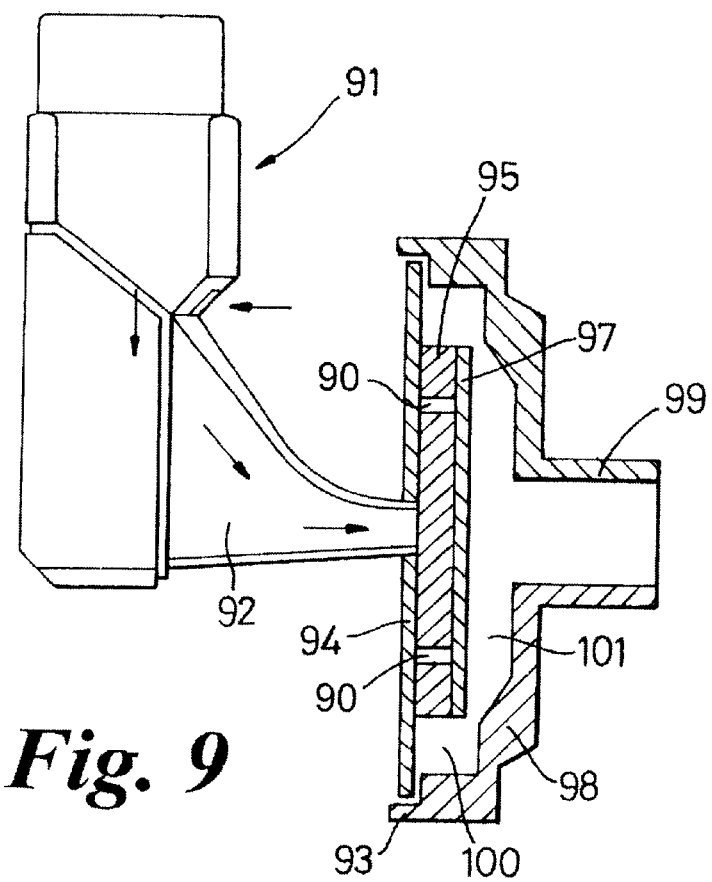
Figure 9A:
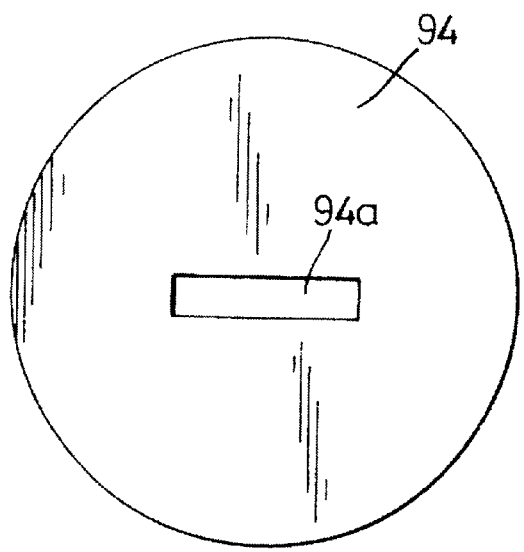
Figure 9C:
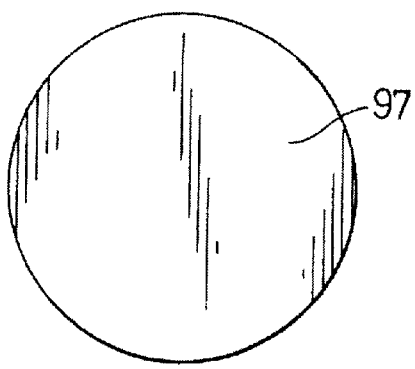
Figure 9B:
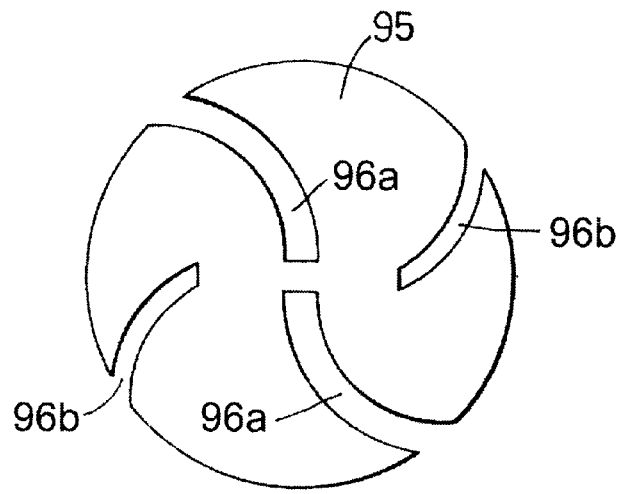
Figure 9D:
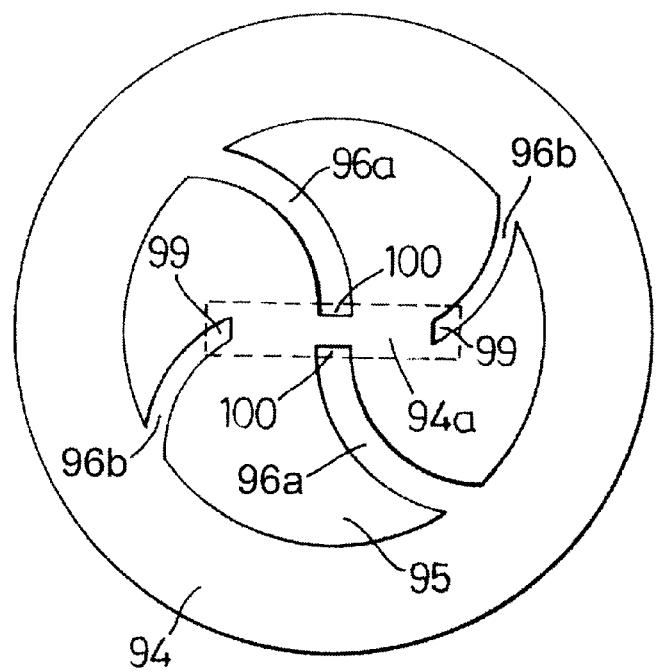

The embodiment of FIG. 9 is simpler in structure than the embodiments of FIGS. 1 and 3, and can be more cheaply manufactured. However, there is more loss of kinetic energy in the embodiment of FIG. 9 due to the flow path having more abrupt changes of direction. This reduces the speed at which the air/powder mixture enters the cyclone chamber 100, and the efficiency of the cyclonic separation of the heavier and lighter particles is correspondingly reduced.

What is claimed is:

1. A dry powder inhaler comprising a body defining a storage chamber for a powder and further defining an inhalation passage through which air is drawn via a mouthpiece, the mouthpiece having an inlet and an outlet and defining a flow duct for the flow of an air/powder mixture therethrough, the flow duct extending between said inlet and said outlet and including a circulatory section in which the flow duct is in the form of one or more passageways, said one or more passageways being circulatory about an axis extending between said inlet and said outlet, and the flow duct further including a cyclone chamber between said circulatory section and said outlet, said circulatory section serving to convert the linear flow of the air/powder mixture entering the mouthpiece into a circulatory flow that causes the powder particles of the air/powder mixture to separate by size, and said cyclone chamber serving to trap the largest powder particles.

2. The inhaler of claim 1 wherein said circulatory section is a helical section in which the flow duct is in the form of one or more passageways of substantially helical conformation.

3. The inhaler of claim 1 wherein said one or more passageways are arranged as a helix or helices about said axis.

4. The inhaler of claim 1 wherein each of said one or more passageways has a cross-sectional area that decreases in a direction from said inlet towards said outlet.

5. The inhaler of claim 2 wherein each of said one or more passageways has a cross-sectional area that decreases in a direction from said inlet towards said outlet.

6. The inhaler of claim 3 wherein each of said one or more passageways has a cross-sectional area that decreases in a direction from said inlet towards said outlet.

\* \* \* \* \*